(12) United States Patent
Riedel

(10) Patent No.: US 11,918,786 B2
(45) Date of Patent: Mar. 5, 2024

(54) MEDICAMENT DELIVERY DEVICE AND ACTUATION MECHANISM FOR A DRUG DELIVERY DEVICE

(71) Applicant: Sanofi-Aventis Deutschland GMBH, Frankfurt am Main (DE)

(72) Inventor: Stephan Riedel, Frankfurt (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 490 days.

(21) Appl. No.: 17/011,607

(22) Filed: Sep. 3, 2020

(65) Prior Publication Data

US 2020/0397992 A1    Dec. 24, 2020

Related U.S. Application Data

(63) Continuation of application No. 16/892,047, filed on Jun. 3, 2020, which is a continuation of application (Continued)

(30) Foreign Application Priority Data

Sep. 23, 2011    (EP) .................................... 11182632

(51) Int. Cl.
*A61M 5/20* (2006.01)
*A61M 5/32* (2006.01)

(52) U.S. Cl.
CPC .............. *A61M 5/20* (2013.01); *A61M 5/321* (2013.01); *A61M 5/3257* (2013.01);
(Continued)

(58) Field of Classification Search
CPC ........ A61M 2005/3267; A61M 5/3202; A61M 2005/2013; A61M 2005/206;
(Continued)

(56) References Cited

U.S. PATENT DOCUMENTS

| 4,378,015 A | 3/1983 | Wardlaw |
| 4,487,602 A | 12/1984 | Christensen et al. |

(Continued)

FOREIGN PATENT DOCUMENTS

| DE | 102004053529 | 5/2006 |
| EP | 1949928 | 7/2008 |

(Continued)

OTHER PUBLICATIONS

PCT International Preliminary Report on Patentability in International Appln. No. PCT/EP2012/068572, dated Mar. 25, 2014, 6 pages.

(Continued)

*Primary Examiner* — Scott J Medway
(74) *Attorney, Agent, or Firm* — Fish & Richardson P.C.

(57) ABSTRACT

Described is an actuation mechanism for a medicament delivery device having a needle with a distal tip. The actuation mechanism comprises an outer sleeve telescopically relative to the delivery device and an inner sleeve telescopically arranged relative to the outer sleeve. The outer sleeve is axially translatable relative to the delivery device, and the inner sleeve is axially translatable relative to the outer sleeve. In a first state, the inner sleeve protrudes distally from the outer sleeve and the outer sleeve protrudes distally from the delivery device. In a second state, the inner sleeve is contained within the outer sleeve. Movement of the outer sleeve proximally relative to the delivery device in the second state initiates delivery of a medicament in the delivery device.

15 Claims, 1 Drawing Sheet

Related U.S. Application Data

No. 15/177,948, filed on Jun. 9, 2016, now Pat. No. 10,675,408, which is a continuation of application No. 14/346,228, filed as application No. PCT/EP2012/068572 on Sep. 20, 2012, now Pat. No. 9,364,617.

(52) U.S. Cl.
CPC .............. *A61M 2005/2013* (2013.01); *A61M 2005/3247* (2013.01); *A61M 2005/3267* (2013.01); *A61M 2205/6081* (2013.01)

(58) Field of Classification Search
CPC ........ A61M 2005/2073; A61M 5/3243; A61M 5/3271; A61M 2205/59; A61M 5/20; A61M 5/3257; A61M 5/46; A61M 2005/201
See application file for complete search history.

(56) References Cited

U.S. PATENT DOCUMENTS

| | | |
|---|---|---|
| 4,897,083 A | 1/1990 | Martell |
| 4,902,279 A | 2/1990 | Schmidtz et al. |
| 5,176,643 A | 1/1993 | Kramer et al. |
| 5,248,301 A | 9/1993 | Koenig, Jr. et al. |
| 5,271,744 A | 12/1993 | Kramer et al. |
| 5,336,199 A | 8/1994 | Castillo et al. |
| 5,451,210 A | 9/1995 | Kramer et al. |
| 5,478,316 A | 12/1995 | Bitdinger et al. |
| 5,599,309 A | 2/1997 | Marshall et al. |
| 5,609,577 A | 3/1997 | Haber et al. |
| 5,658,259 A | 8/1997 | Pearson et al. |
| 5,681,291 A | 10/1997 | Galli |
| 6,099,503 A | 8/2000 | Stradella |
| 6,099,504 A | 8/2000 | Gross et al. |
| 6,102,896 A | 8/2000 | Roser |
| 6,162,197 A | 12/2000 | Mohammad |
| 6,280,421 B1 | 8/2001 | Kirchhofer et al. |
| 6,575,939 B1 | 6/2003 | Brunel |
| 6,767,336 B1 | 7/2004 | Kaplan |
| 7,083,600 B2 | 8/2006 | Meloul |
| 7,147,624 B2 | 12/2006 | Hirsiger et al. |
| 7,361,160 B2 | 4/2008 | Hommann et al. |
| 7,540,858 B2 | 6/2009 | Dibiasi |
| 7,635,348 B2 * | 12/2009 | Raven ................. A61M 5/3202 604/193 |
| 7,749,195 B2 | 7/2010 | Hommann |
| 8,029,458 B2 | 10/2011 | Cherif-Cheikh et al. |
| 8,277,414 B2 | 10/2012 | Barrow-Williams et al. |
| 8,313,463 B2 | 11/2012 | Barrow-Williams et al. |
| 8,366,669 B2 | 2/2013 | Donald et al. |
| 8,500,693 B2 | 8/2013 | Maritan |
| 8,632,503 B2 | 1/2014 | Ruan et al. |
| 8,696,625 B2 | 4/2014 | Carrel et al. |
| 8,945,049 B2 | 2/2015 | Hommann et al. |
| 9,028,453 B2 | 5/2015 | Jennings |
| 9,072,833 B2 | 7/2015 | Jennings et al. |
| 9,095,288 B2 | 8/2015 | Crawford et al. |
| 9,125,985 B2 | 9/2015 | Adams et al. |
| 9,149,574 B2 | 10/2015 | Hornig et al. |
| 9,364,610 B2 | 6/2016 | Kramer et al. |
| 9,364,617 B2 | 6/2016 | Riedel |
| 9,682,198 B2 | 6/2017 | Vedrine et al. |
| 9,687,607 B2 | 6/2017 | Brereton et al. |
| 9,764,091 B2 | 9/2017 | Bechmann et al. |
| 9,931,467 B2 | 4/2018 | Fabien et al. |
| 9,931,471 B2 | 4/2018 | Ekman et al. |
| 10,022,506 B2 | 7/2018 | Pribitkin |
| 10,232,117 B2 | 3/2019 | Halseth |
| 10,279,127 B2 | 5/2019 | Henderson et al. |
| 10,406,288 B2 | 9/2019 | Reber et al. |
| 10,675,408 B2 | 6/2020 | Riedel |
| 2001/0031949 A1 | 10/2001 | Asbaghi |
| 2003/0050606 A1 | 3/2003 | Brand et al. |
| 2003/0120209 A1 * | 6/2003 | Jensen ..................... G09F 1/04 604/110 |
| 2003/0168366 A1 | 9/2003 | Hirsiger et al. |
| 2003/0212362 A1 | 11/2003 | Roser |
| 2004/0102740 A1 | 5/2004 | Meloul |
| 2004/0225262 A1 | 11/2004 | Fathallah et al. |
| 2005/0113750 A1 | 5/2005 | Targell |
| 2005/0171486 A1 | 8/2005 | Hochman |
| 2005/0203466 A1 | 9/2005 | Hommann et al. |
| 2005/0288607 A1 | 12/2005 | Konrad |
| 2006/0224124 A1 | 10/2006 | Scherer |
| 2006/0270984 A1 * | 11/2006 | Hommann ............ A61M 5/347 604/134 |
| 2007/0027430 A1 | 2/2007 | Hommann |
| 2007/0129674 A1 | 6/2007 | Liversidge |
| 2007/0173772 A1 | 7/2007 | Liversidge |
| 2008/0319346 A1 | 12/2008 | Crawford et al. |
| 2009/0270804 A1 * | 10/2009 | Mesa ..................... A61M 5/24 604/111 |
| 2010/0049125 A1 | 2/2010 | James et al. |
| 2010/0137801 A1 | 6/2010 | Streit et al. |
| 2010/0234811 A1 | 9/2010 | Schubert et al. |
| 2011/0092915 A1 | 4/2011 | Olson et al. |
| 2011/0257603 A1 | 10/2011 | Ruan et al. |
| 2011/0288491 A1 | 11/2011 | Newman et al. |
| 2012/0150125 A1 | 6/2012 | Karlsson et al. |
| 2012/0220954 A1 | 8/2012 | Cowe |
| 2013/0110050 A1 | 5/2013 | Boyd et al. |
| 2013/0289481 A1 | 10/2013 | Roberts et al. |
| 2014/0236094 A1 | 8/2014 | Riedel |
| 2015/0250954 A1 | 9/2015 | Keitzmann et al. |
| 2016/0287787 A1 | 10/2016 | Riedel |

FOREIGN PATENT DOCUMENTS

| | | |
|---|---|---|
| JP | H6-508773 | 10/1994 |
| JP | 2008-536597 | 9/2008 |
| JP | 2008-246190 | 10/2008 |
| JP | 2013-534164 | 9/2013 |
| WO | WO 1992/019296 | 11/1992 |
| WO | WO 1994/21316 | 9/1994 |
| WO | WO 2003/077968 | 9/2003 |
| WO | WO 2006/111861 | 10/2006 |
| WO | WO 2006/111862 | 10/2006 |
| WO | WO 2011/047298 | 4/2011 |
| WO | WO 2011/048422 | 4/2011 |
| WO | WO 2012/022810 | 2/2012 |

OTHER PUBLICATIONS

PCT International Search Report and Written Opinion in International Appln. No. PCT/EP2012/068572, dated Nov. 26, 2012, 8 pages.

Third Party Observations filed in European Appln. No. 17166144.0, dated Sep. 7, 2022, 7 pages.

* cited by examiner

MEDICAMENT DELIVERY DEVICE AND ACTUATION MECHANISM FOR A DRUG DELIVERY DEVICE

CROSS REFERENCE TO RELATED APPLICATIONS

The present application is a continuation of U.S. patent application Ser. No. 16/892,047, filed Jun. 3, 2020, which is a continuation of U.S. patent application Ser. No. 15/177, 948, filed Jun. 9, 2016, now U.S. Pat. No. 10,675,408, which is a continuation of U.S. patent application Ser. No. 14/346, 228, filed Mar. 20, 2014, now U.S. Pat. No. 9,364,617, which is a U.S. National Phase Application pursuant to 35 U.S.C. § 371 of International Application No. PCT/EP2012/068572 filed Sep. 20, 2012, which claims priority to European Patent Application No. 11182632.7 filed Sep. 23, 2011. The entire disclosure contents of these applications are herewith incorporated by reference into the present application.

FIELD OF INVENTION

The invention relates to a medicament delivery device and an actuation mechanism for a medicament delivery device.

BACKGROUND

Conventional medicament delivery devices containing a selected dose of a medicament are well-known devices for administering the medicament to a patient. A conventional delivery device comprises a needle to administer the medicament. Safety devices for covering a needle of the delivery device before and after use are also well known. In a conventional safety device, a needle shield is moved either manually or automatically (i.e., by spring) to cover the needle.

A specific type of a medicament delivery device is an autoinjector, which equipped with an actuation button to actuate automatic delivery of the medicament. To administer the medicament, the autoinjector is pressed against an injection site, which retracts the needle shield. When the actuation button is pressed, the needle is inserted into the injection site and the medicament is administered. The conventional delivery device, thus, requires two acts—pressing of the delivery device to injection site and pressing the actuation button. It may be difficult to perform either or both of these acts when the patient/operator has lessened dexterity, e.g., due to age, disability, illness, sensory deficiency, etc.

Other conventional delivery devices are actuated upon contact with the injection site. These devices are pressed against the injection site, which retracts the needle shield, and pressed with enhanced force to initiate delivery of the medicament. However, patients may be confused by these types of delivery devices, because there is no actuation button.

SUMMARY

It is an object of the present invention to provide an actuation mechanism for a medicament delivery device for easy and safe medicament delivery.

In an exemplary embodiment, an actuation mechanism for a medicament delivery device has a needle with a distal tip. The actuation mechanism comprises an outer sleeve telescopically relative to the delivery device and an inner sleeve telescopically arranged relative to the outer sleeve. The outer sleeve is axially translatable relative to the delivery device, and the inner sleeve is axially translatable relative to the outer sleeve. In a first state, the inner sleeve protrudes distally from the outer sleeve and the outer sleeve protrudes distally from the delivery device. In a second state, the inner sleeve is contained within the outer sleeve. Movement of the outer sleeve proximally relative to the delivery device in the second state initiates delivery of a medicament in the delivery device.

In an exemplary embodiment, the inner sleeve and the outer sleeve have different colors or indicia.

In an exemplary embodiment, the actuation mechanism further comprises a first spring element biasing the inner sleeve in a distal direction relative to the outer sleeve. The actuation mechanism further comprises a second spring element biasing the outer sleeve in a distal direction relative to the delivery device. The second spring element is a harder compression spring than the first spring element.

In an exemplary embodiment, the outer sleeve is positionally fixed relative to the delivery device in the first state. The inner sleeve engages the outer sleeve in the second state. The inner sleeve includes a latch adapted to engage a recess or opening in the outer sleeve. The outer sleeve includes a latch adapted to engage a recess or opening in the inner sleeve.

In an exemplary embodiment, when in a third state, the inner sleeve is locked relative to the outer sleeve and the outer sleeve is locked relative to the delivery device.

In an exemplary embodiment, a drug delivery device comprises an actuation mechanism according to any one of the exemplary embodiments described above, and further includes a needle having a distal tip. In the first state, the inner sleeve and/or the outer sleeve cover the distal tip, and in the second state, the distal tip is adapted to protrude distally relative to the outer sleeve. In the third state, the inner sleeve and/or the outer sleeve cover the distal tip of the needle.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(0)14, Asp28] Exendin-4(1-39),
des Pro36 [Met(0)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(0)14 Trp(02)25, Asp28] Exendin-4(1-39),
des Pro36 [Met(0)14 Trp(02)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4(1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
(Lys)6-des Pro36 [Met(0)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(0)14, Asp28] Exendin-4(1-39)-NH2,
H-Asn-(Glu)5-des Pro36, Pro37, Pro38 [Met(0)14, Asp28] Exendin-4(1-39)-NH2,
des Pro36, Pro37, Pro38 [Met(0)14, Asp28] Exendin-4(1-39)-(Lys)6-NH2,
H-(Lys)6-des Pro36, Pro37, Pro38 [Met(0)14, Asp28] Exendin-4(1-39)-(Lys)6-NH2,
H-Asn-(Glu)5 des Pro36, Pro37, Pro38 [Met(0)14, Asp28] Exendin-4(1-39)-(Lys)6-NH2,
H-Lys6-des Pro36 [Met(0)14, Trp(02)25, Asp28] Exendin-4(1-39)-Lys6-NH2,
H-des Asp28 Pro36, Pro37, Pro38 [Met(0)14, Trp(02)25] Exendin-4(1-39)-NH2,
H-(Lys)6-des Pro36, Pro37, Pro38 [Met(0)14, Asp28] Exendin-4(1-39)-NH2,
H-Asn-(Glu)5-des Pro36, Pro37, Pro38 [Met(0)14, Trp(02)25, Asp28] Exendin-4(1-39)-NH2,
des Pro36, Pro37, Pro38 [Met(0)14, Trp(02)25, Asp28] Exendin-4(1-39)-(Lys)6-NH2,
H-(Lys)6-des Pro36, Pro37, Pro38 [Met(0)14, Trp(02)25, Asp28] Exendin-4(S1-39)-(Lys)6-NH2,
H-Asn-(Glu)5-des Pro36, Pro37, Pro38 [Met(0)14, Trp(02)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins, which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus, are not limitive of the present invention, and wherein.

Corresponding parts are marked with the same reference symbols in all figures.

DETAILED DESCRIPTION

Figure 1:
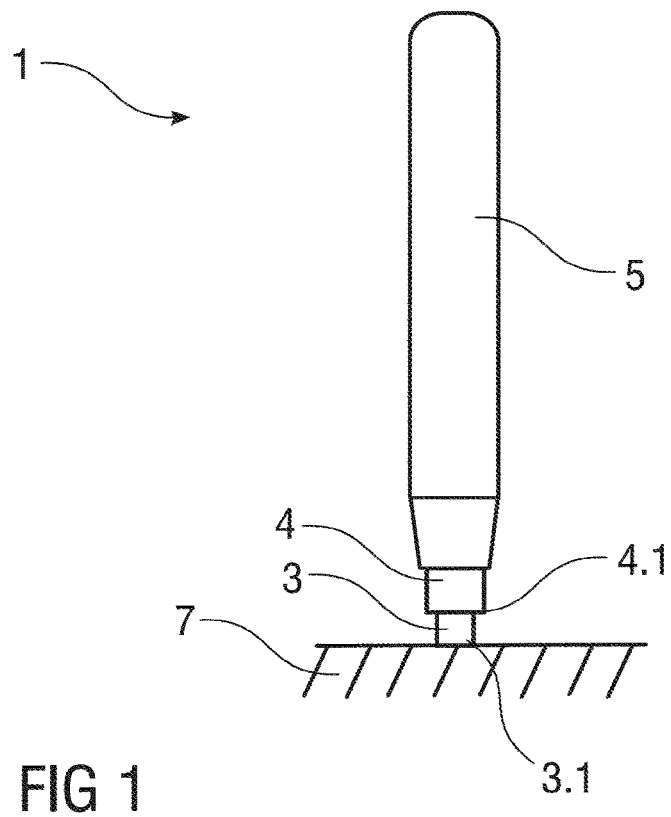
FIG. 1 shows an exemplary embodiment of a medicament delivery device before use.
Figure 2:
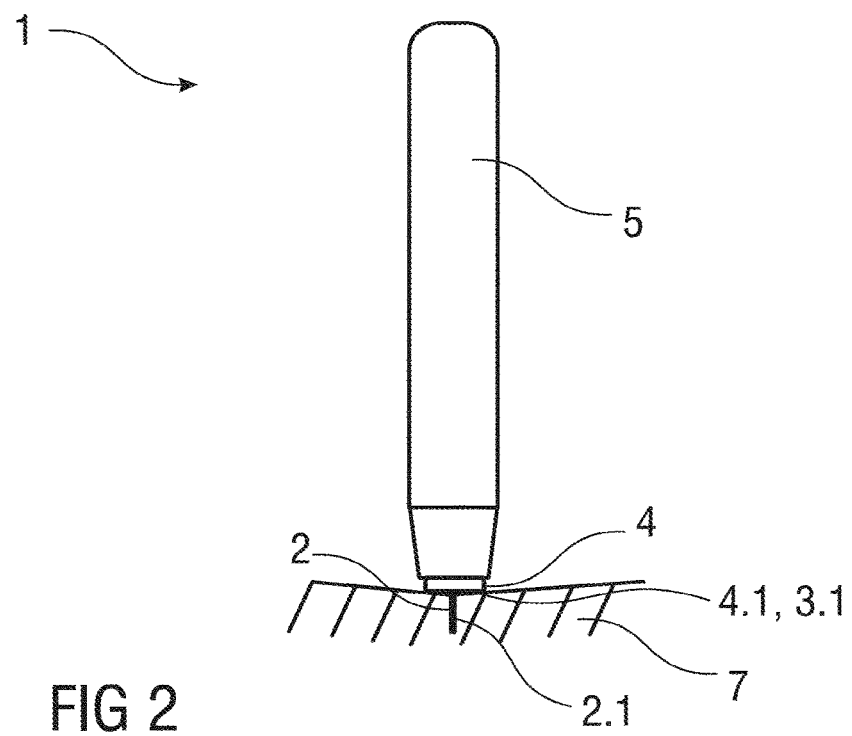
FIG. 2 shows an exemplary embodiment of a medicament delivery device during use.

FIGS. 1 and 2 show an exemplary embodiment of a medicament delivery device 1 before and during administration of a medicament to a patient, respectively. Those of skill in the art will understand that the patient may be a human or animal. In the exemplary embodiment, the delivery device 1 is an autoinjector designed to automatically deliver a dose of a medicament by means of a needle 2 upon sleeve-driven actuation. Those of skill in the art will understand that the delivery device 1 may be a pen injector, a syringe, an infusion device, etc.

An exemplary embodiment of a sleeve-driven actuation mechanism comprises a housing 5, an inner sleeve 3 and an outer sleeve 4 telescopically arranged on the inner sleeve 3. The inner sleeve 3 and the outer sleeve 4 are axially translatable relative to each other and relative to the housing 5. The inner sleeve 3 covers the needle 2 before and after use of the delivery device 1 to prevent accidental needlestick injuries. The outer sleeve 4 serves to actuate a delivery mechanism in the delivery device 1. The sleeves 3, 4 may be arranged telescopically and substantially shaped as hollow cylinders with open proximal ends. The outer sleeve 4 has an open distal end 4.1 for accommodating the inner sleeve 3. A distal end 3.1 of the inner sleeve 3 may be opened or have a cover face with a central aperture for accommodating projection of the needle 2. In an exemplary embodiment, the distal end 3.1 of the inner sleeve 3 may be planar or curved.

FIG. 1 shows an exemplary embodiment of the delivery device 1 in a first state, e.g., prior to use on an injection site 7. In the first state, the outer sleeve 4 projects distally out of the housing 5, and the inner sleeve 3 projects distally out of the outer sleeve 4. In the first state, the sleeves 3, 4 cover a distal needle tip 2.1 of the needle 2 and thus prevent accidental needlestick injuries. For example, in the first state, the distal needle tip 2.1 of the needle 2 may be proximal of the distal end 4.1 of the outer sleeve 4.

In an exemplary embodiment, in the first state, the inner sleeve 3 may be axially translatable relative to the outer sleeve 4, but the outer sleeve 4 may be locked relative to the housing 5. Thus, the inner sleeve 3 may be repeatedly retracted into the outer sleeve 4 a predetermined distance without triggering delivery of the medicament. This may prevent inadvertent triggering of the delivery device 1, allowing for realignment of the delivery device 1 on a different injection site.

In an exemplary embodiment, the inner sleeve 3 may be biased in the first state by a first spring element, and the outer sleeve 4 may be biased in the first state by a second spring element.

FIG. 2 shows an exemplary embodiment of the delivery device 1 in a second state, e.g., during use. When the delivery device 1 is pressed against an injection site, the inner sleeve 3 may be pushed into an intermediate position in which it is fully contained inside the outer sleeve 4, and the distal end 4.1 of the outer sleeve 4 touches the injection site 7. When the distal end 3.1 of the inner sleeve 3 is in a same plane as the distal end 4.1 of the outer sleeve 4, the inner sleeve 3 and the outer sleeve 4 may be coupled together so that further pressing of the delivery device 1 against the injection site 7 causes the sleeves 3, 4 to move together proximally relative to the housing 5. For example, the inner sleeve 3 may engage the outer sleeve 4 when the inner sleeve 3 has attained a predetermined axial position relative to the outer sleeve 4.

In an exemplary embodiment, when the inner sleeve 3 engages the outer sleeve 4, the needle 2 may be inserted into the injection site 7 and the medicament may be delivered. In another exemplary embodiment, when the outer sleeve 4 is pressed against the injection site 7, the needle 2 may be inserted into the injection site 7 and the medicament may be delivered.

A tactile feedback may be provided in the form of resistance. For example, the first spring element associated with the inner sleeve 3 may require less force to compress than the second spring element associated with the outer sleeve 4. Thus, an increased force may be necessary to cause the outer sleeve 4 to move proximally, axially relative to the housing 5. This has the advantage that the patient can clearly distinguish the two steps of the process and thus removes a potential patient's feeling of insecurity concerning the injection process. A further advantage of the actuation mechanism according to the invention is that the different pressures for the two steps of the process can be realized more easily because they are induced automatically by coupling the sleeves to different compression springs. Of course, in alternative embodiments, the compression springs may be replaced by other tensioning members.

In an exemplary embodiment, the sleeves 3, 4 have different colors or indicia. For example, different colors emphasize the different functions of the sleeves 3, 4 and thus distinguish the two steps of the injection process even more clearly.

After the injection process, the delivery device 1 is withdrawn from the injection site 7. When force is removed from the sleeves 3,4, the compression springs relax and shift the sleeves 3, 4 distally toward the first state so that they again cover the needle 2. Thus, advantageously accidental needlestick injuries are prevented after use of the delivery device 1.

In a preferred extension of the invention, the delivery device 1 additionally comprises additionally a locking mechanism, which locks the position of the inner sleeve 3 and/or the position of the outer sleeve 4 relative to each other and/or the housing 5. The locking mechanism may ensure that the inner sleeve 3 and/or outer sleeve 4 cover the distal needle tip 2.1. This advantageously further reduces the risk of accidental needlestick injuries after using the delivery device 1.

For instance, the locking mechanism may comprise at least one latch member of the inner sleeve 3 or the outer sleeve 4 and a corresponding groove located in the housing 5 of the drug delivery device 1, the groove being adapted to receive the latch member. Alternatively, the latch member may be part of the housing 5 and the groove may be located in a sleeve 3, 4.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
   a housing;
   a needle comprising a distal tip through which a dose of medicament is deliverable from the medicament delivery device into an injection site, wherein at least a portion of the needle extends distally out of the housing;
   a sleeve assembly coupled to the housing, the sleeve assembly being adjacent to the needle, the sleeve assembly being movable during an injection process between a first position in which the sleeve assembly covers the portion of the needle extending distally out of the housing and a second position in which the needle at least partially extends distally beyond the sleeve assembly, wherein the sleeve assembly comprises a first sleeve and a second sleeve telescopically movable relative to one another;
   one or more indicia on the sleeve assembly, the one or more indicia being configured to provide an indication of progress of the injection process, wherein the one or more indicia comprise a first indicia on the first sleeve and a second indicia on the second sleeve, the first indicia being different from the second indicia; and
   a first biasing element configured to bias the first sleeve away from the housing; and
   a second biasing element configured to bias the second sleeve away from the housing,
   wherein the first biasing element and the second biasing element are configured such that a force needed to compress the first biasing element is less than a force needed to compress the second biasing element.

2. The medicament delivery device of claim 1, wherein:
   when the sleeve assembly is in the first position, the sleeve assembly is movable to an intermediate position as the medicament delivery device is pressed against the injection site in a first step of the injection process, and when the sleeve assembly is in the intermediate position, the needle is configured to be inserted into the injection site as the medicament delivery device is further pressed against the injection site in a second step of the injection process.

3. The medicament delivery device of claim 2, wherein the indication of progress of the injection process is indicative of the first step of the injection process and the second step of the injection process.

4. The medicament delivery device of claim 1, wherein the indication of progress of the injection process comprises:
a first indication of a first step in the injection process in which the sleeve assembly moves relative to the injection site before the needle is inserted into the injection site, and
a second indication of a second step in the injection process in which the sleeve assembly moves relative to the injection site after the needle is inserted into the injection site.

5. The medicament delivery device of claim 1, wherein the one or more indicia comprise a color.

6. The medicament delivery device of claim 5, wherein the color is a first color on a first portion of the sleeve assembly, and the one or more indicia comprise a second color on a second portion of the sleeve assembly.

7. The medicament delivery device of claim 1, further comprising one or more springs configured to bias the sleeve assembly toward the first position.

8. The medicament delivery device of claim 1, wherein the sleeve assembly comprises a hollow cylindrical member.

9. The medicament delivery device of claim 8, wherein the sleeve assembly comprises an outer surface comprising a proximal portion and a distal portion,
wherein the proximal portion and the distal portion of the outer surface of the sleeve assembly are configured to
be exposed outside of the housing when the sleeve assembly is in the first position, and
be concealed within the housing when the sleeve assembly is in the second position.

10. The medicament delivery device of claim 9, wherein the sleeve assembly is movable from the first position to an intermediate position, and from the intermediate position to the second position, wherein the sleeve assembly is configured to cover the needle in the intermediate position, and
wherein only one of the proximal portion and the distal portion is configured to be exposed outside of the medicament delivery device when the sleeve assembly is in the intermediate position.

11. The medicament delivery device of claim 1, wherein an outer surface of the first sleeve and an outer surface of the second sleeve are configured to be exposed outside of the housing when the sleeve assembly is in the first position, and to be concealed within the housing when the sleeve assembly is in the second position.

12. The medicament delivery device of claim 11,
wherein the sleeve assembly is movable from the first position to an intermediate position, and from the intermediate position to the second position, wherein the sleeve assembly is configured to cover the needle in the intermediate position, and wherein the outer surface of the first sleeve and the outer surface of the second sleeve are configured such that the outer surface of the second sleeve is concealed within the first sleeve and the outer surface of the first sleeve is exposed outside of the housing when the sleeve assembly is in the intermediate position.

13. The medicament delivery device of claim 1, wherein the sleeve assembly comprises a first and second portions comprising the one or more indicia such that the first and second portions of the sleeve assembly are visually distinguishable from one another.

14. A medicament delivery device comprising:
a housing;
a needle comprising a distal tip through which a dose of medicament is deliverable from the medicament delivery device into an injection site, wherein at least a portion of the needle extends distally out of the housing;
a sleeve assembly coupled to the housing, the sleeve assembly being adjacent to the needle, the sleeve assembly comprising a first portion and a second portion, the sleeve assembly being movable in a proximal direction from a first position to an intermediate position during an injection process, and from the intermediate position to a second position during the injection process,
wherein in the first position, the sleeve assembly extends distally from the housing and beyond the portion of the needle such that the first portion and the second portion of the sleeve assembly are exposed outside of the housing,
wherein in the intermediate position, the sleeve assembly extends distally from the housing such that the first portion is exposed outside of the medicament delivery device, and the second portion is concealed within the medicament delivery device,
wherein the first portion and the second portion of the sleeve assembly are telescopically movable relative to one another, and
wherein in the second position, the portion of the needle extends beyond the sleeve assembly and the first and second portions of the sleeve assembly are concealed within the housing;
one or more indicia on the sleeve assembly, the one or more indicia being configured to provide an indication of progress of the injection process, wherein the one or more indicia comprise a first indicia on the first portion and a second indicia on the second portion, the first indicia being different from the second indicia; and
a first biasing element configured to bias the first portion away from the housing, and
a second biasing element configured to bias the second portion away from the housing,
wherein the first biasing element and the second biasing element are configured such that a force needed to compress the first biasing element is less than a force needed to compress the second biasing element.

15. The medicament delivery device of claim 14, wherein the first portion of the sleeve assembly is a proximal portion of the sleeve assembly, and the second portion of the sleeve assembly is a distal portion of the sleeve assembly.

* * * * *

UNITED STATES PATENT AND TRADEMARK OFFICE
CERTIFICATE OF CORRECTION

| | | |
|---|---|---|
| PATENT NO. | : 11,918,786 B2 | Page 1 of 1 |
| APPLICATION NO. | : 17/011607 | |
| DATED | : March 5, 2024 | |
| INVENTOR(S) | : Stephan Riedel | |

It is certified that error appears in the above-identified patent and that said Letters Patent is hereby corrected as shown below:

In the Claims

In Column 10, Line 46 (approx.), Claim 14, after "indicia" delete "being"

Signed and Sealed this
Thirtieth Day of April, 2024

Katherine Kelly Vidal
*Director of the United States Patent and Trademark Office*